(12) United States Patent
Shaver

(10) Patent No.: US 7,902,397 B2
(45) Date of Patent: Mar. 8, 2011

(54) METHOD AND APPARATUS FOR MAKING ACETIC ACID WITH IMPROVED PRODUCTIVITY

(75) Inventor: Ronald David Shaver, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 698 days.

(21) Appl. No.: 11/974,106

(22) Filed: Oct. 11, 2007

(65) Prior Publication Data

US 2009/0099389 A1    Apr. 16, 2009

(51) Int. Cl.
*C07C 51/10* (2006.01)
*C07C 51/12* (2006.01)

(52) U.S. Cl. ............... 562/517; 562/519; 562/608

(58) Field of Classification Search ............ None
See application file for complete search history.

(56) References Cited

U.S. PATENT DOCUMENTS

| | | | |
|---|---|---|---|
| 5,144,068 A | 9/1992 | Smith et al. | 562/519 |
| 5,750,007 A * | 5/1998 | Clode et al. | 203/3 |
| 5,877,347 A | 3/1999 | Ditzel et al. | 562/519 |
| 5,877,348 A | 3/1999 | Ditzel et al. | 562/519 |
| 5,883,295 A | 3/1999 | Sunley et al. | 562/519 |
| 6,642,413 B2 | 11/2003 | Thiebaut | 562/517 |

OTHER PUBLICATIONS

Applied Homogeneous Catalyst With Organometallic Compounds, Cornils et al., Ed. (Bench Edition) (Wylie, Weinheim, Federal Republic of Germany 2000), Chapter 2, Parts 2.1.2, and following, pp. 104-137.

* cited by examiner

*Primary Examiner* — Paul A Zucker

(57) ABSTRACT

An improved apparatus and method of producing acetic acid includes recovering product from the residue of a light ends column and feeding the acid so recovered forward in order to increase system productivity. Load on the light ends column is reduced and load on a dehydrating column may also be lessened in a preferred embodiment where the recovered acid is fed forward without further water removal.

18 Claims, 4 Drawing Sheets

_US 7,902,397 B2_

METHOD AND APPARATUS FOR MAKING ACETIC ACID WITH IMPROVED PRODUCTIVITY

TECHNICAL FIELD

The present invention relates generally to an apparatus and method for producing acetic acid wherein product is recovered from the residue of a light ends column and fed forward in order to increase system productivity.

BACKGROUND ART

Carbonylation processes are well known in the art. Of particular commercial significance are processes for the carbonylation of methanol to make acetic acid and processes for the carbonylation of methyl acetate to make acetic anhydride. See Applied Homogeneous Catalyst With Organometallic Compounds, Cornils et al., Ed. (Bench Edition) (Wylie, Weinheim, Federal Republic of Germany 2000), Chapter 2, Parts 2.1.2 and following, pp. 104-137. See, also, U.S. Pat. No. 6,642,413 to Thiebaut.

To make acetic acid, one method of choice involves carbonylating methanol in a homogeneous reaction medium wherein rhodium is utilized as a catalyst. Generally, the reaction medium includes catalyst, water, acetic acid, dissolved carbon monoxide (CO), methanol, methyl acetate (MeAc), hydriodic acid (HI), methyl iodide and optionally one or more promoters and/or stabilizers. Methanol and carbon monoxide are fed to a reactor as feedstocks. A portion of the reaction medium is continuously withdrawn and provided to a flasher where product is flashed off and sent (as vapor) to a purification train. The purification train includes a light ends column which removes "light" or low boiling components as overhead and provides a product stream for further purification. A particularly preferred carbonylation process is taught in U.S. Pat. No. 5,144,068 to Smith et al. In this so called "low water" process, an alcohol such as methanol is reacted with carbon monoxide in a liquid reaction medium containing a rhodium catalyst stabilized with an iodide salt, especially lithium iodide along with methyl iodide and methyl acetate in specified proportions. With a finite concentration of water in the reaction medium, the product is the carboxylic acid instead of, for example, the anhydride. The reaction system of the '068 patent not only provides an acid product of unusually low water content at unexpectedly favorable rates, but also exhibits unexpectedly high catalyst stability. That is, the catalyst is resistant to catalyst precipitation out of the reaction medium.

Another method of choice for carbonylating methanol involves utilizing a homogeneous iridium catalyst in the reactor. There is disclosed, for example, in U.S. Pat. No. 5,883,295, to Sunley et al. a process for the production of acetic acid comprising carbonylating with carbon monoxide methanol and/or a reactive derivative thereof, in the substantial absence of a metal promoter and/or ionic iodide co-promoter in a carbonylation reactor containing a liquid reaction composition with an iridium carbonylation catalyst, methyl iodide co-catalyst, water, acetic acid, and methyl acetate wherein there is maintained in the liquid reaction composition: (a) water at a concentration of less than 5% by weight; (b) methyl iodide in a concentration of greater than 12% by weight; and (c) in the carbonylation reactor a total pressure of less than 50 bar. See, also, U.S. Pat. No. 5,877,348 to Ditzel et al. and U.S. Pat. No. 5,877,347 also to Ditzel et al.

A frequent production limitation in the purification section of an acetic acid unit is the light ends column. A typical acetic acid carbonylation unit is operated such that product is drawn from the light ends column as a sidestream and the light ends column liquid residue is recycled to the reactor. The residue also contains Rh and Li that is scrubbed out of the vapor feed to the light ends column. In a conventional system, the light ends residue is cooled and then recycled to the base of a flasher where it is pumped back to the reactor by the catalyst recycle pumps. The acetic acid in this residue stream thus represents a recycle of acid that adds hydraulic load to the light ends column.

SUMMARY OF INVENTION

The present invention involves treating the light ends residue stream to separate a portion of the acetic acid from the residue stream and reduce the amount of acid that is recycled to the reaction system. A unit is preferably operated such that the column residue flow is mainly acetic acid with small amounts of MeI, MeAc, and water. This treatment can be done in several ways. First, the light ends column residue can be flashed into a vessel maintained under vacuum. Simulations show that flashing the residue stream to a pressure of 5 psia would allow recovery of ~50% of the acid present in the residue stream, and the resulting temperature of the flash vessel may be, for example, about 185° F. A larger percentage of the acetic acid is removed from the residue stream by operating at an even lower vacuum. The vapor stream from the vacuum flash vessel could be condensed and fed to the drying or dehydration column along with the light ends column sidestream or compressed by a compressor (used to provide the vacuum) and fed to the drying column as a hot vapor.

In another embodiment, the light ends column residue stream is processed in a small distillation column which separates the light components (MeI, MeAc, and water) overhead, returns a concentrated residue to the reaction system, and recovers acetic acid as a sidestream product. The sidestream product is then combined with the drying column residue as specification grade product if sufficiently purified. Otherwise, the sidestream product is fed to the drying column.

The advantages of the present invention are appreciated by reference to FIG. 1 which is a graphical representation showing the fraction of acid recovered from the light ends residue stream and impact on column loading. In FIG. 1 it is seen that more than 40% of the acid in the residue stream of the light ends column can be recovered by simply flashing the stream and that light ends column hydraulic load is substantially reduced at a given production rate.

Further features and advantages of the present invention are discussed below.

BRIEF DESCRIPTION OF DRAWINGS

The invention is described in detail below with reference to the following drawings wherein like numerals designate similar parts and wherein.

DESCRIPTION OF THE PREFERRED EMBODIMENTS

Figure 1:
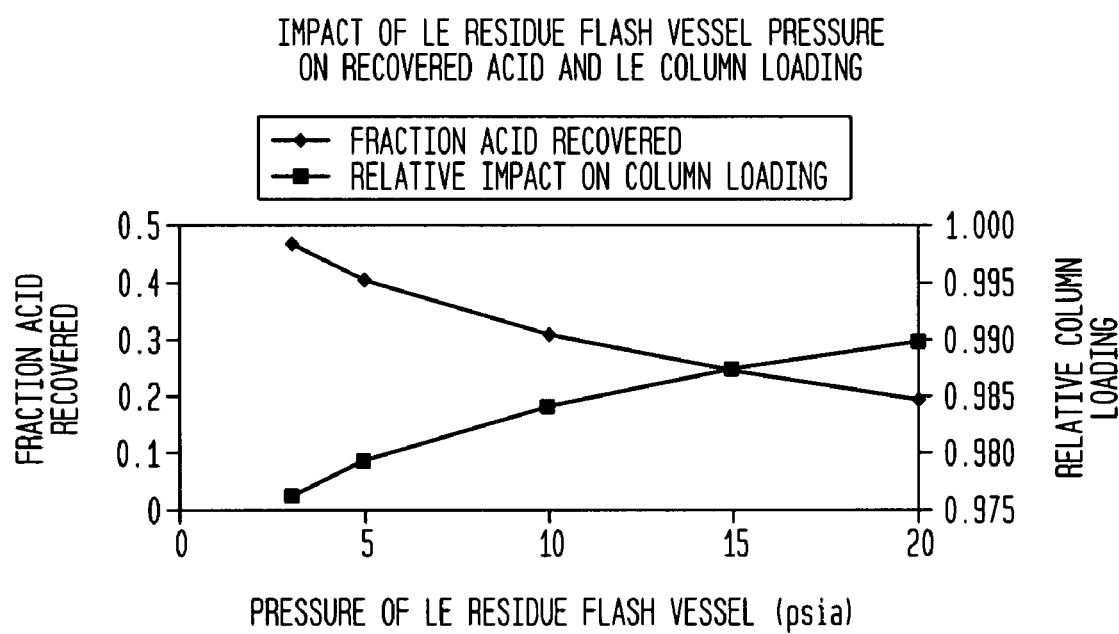
FIG. 1 is a graph showing the effect of using a flash vessel on the light ends residue stream on acid recovery and hydraulic loading of the light ends column.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppb and like terms refer to weight percent, parts per billion by weight and so forth, unless otherwise indicated.

"Distillation column" and like terminology refers to purification equipment which vaporizes liquid (or at least a portion thereof), at least in part, through application of heat to the liquid.

"Distilling" and like terminology refers to at least partial purification of a liquid using a distillation column.

"Flasher vessel" and like terminology refers to a vessel adapted to vaporize liquid, at least in part, through a reduction in pressure as opposed to application of heat. Equipment which vaporizes at least a portion of a liquid through both application of heat and reduction in pressure is considered a distillation column for present purposes.

"Flash", "flashing" and so forth refers to vaporizing liquid by reduction in pressure.

A "stripper" or "stripper column" or like terminology refers to a vessel which receives a liquid stream at or near the top of the vessel from a separate piece of equipment as opposed to a column which refluxes its own condensed distillate.

The Group VIII catalyst may be a rhodium and/or iridium catalyst. The rhodium metal catalyst may be added in any suitable form such that rhodium is in the catalyst solution as an equilibrium mixture including $[Rh(CO)_2I_2]^-$ anion as is well known in the art. Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding rhodium catalysis and iodide salt generation, see U.S. Pat. Nos. 5,001,259 to Smith et al.; 5,026,908 to Smith et al.; and 5,144,068, also to Smith et al., the disclosures of which are hereby incorporated by reference.

Similarly, an iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates, and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

An alkyl halide co-catalyst/promoter is generally used in combination with the Group VIII metal catalyst component. Methyl iodide is preferred as the alkyl halide promoter. Preferably, the concentration of alkyl halide in the liquid reaction composition is in the range 1 to 50% by weight, preferably 2 to 30% by weight.

The alkyl halide promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention includes generally at least a reactive section, and a purification section. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water, and optionally an iodide salt. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water, and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 Bar, preferably 1 to 35 Bar, and most preferably 1 to 15 Bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 Bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed. The crude vapor product stream from the flasher is sent to a purification system which generally includes at least a light ends column and a dehydration column. Carbonylation system may use only 2 purification columns and is preferably operated as described in more detail in U.S. Pat. No. 6,657,078 to Scates et al., entitled "Low Energy Carbonylation Process", the disclosure of which is incorporated herein by reference.

Figure 2:
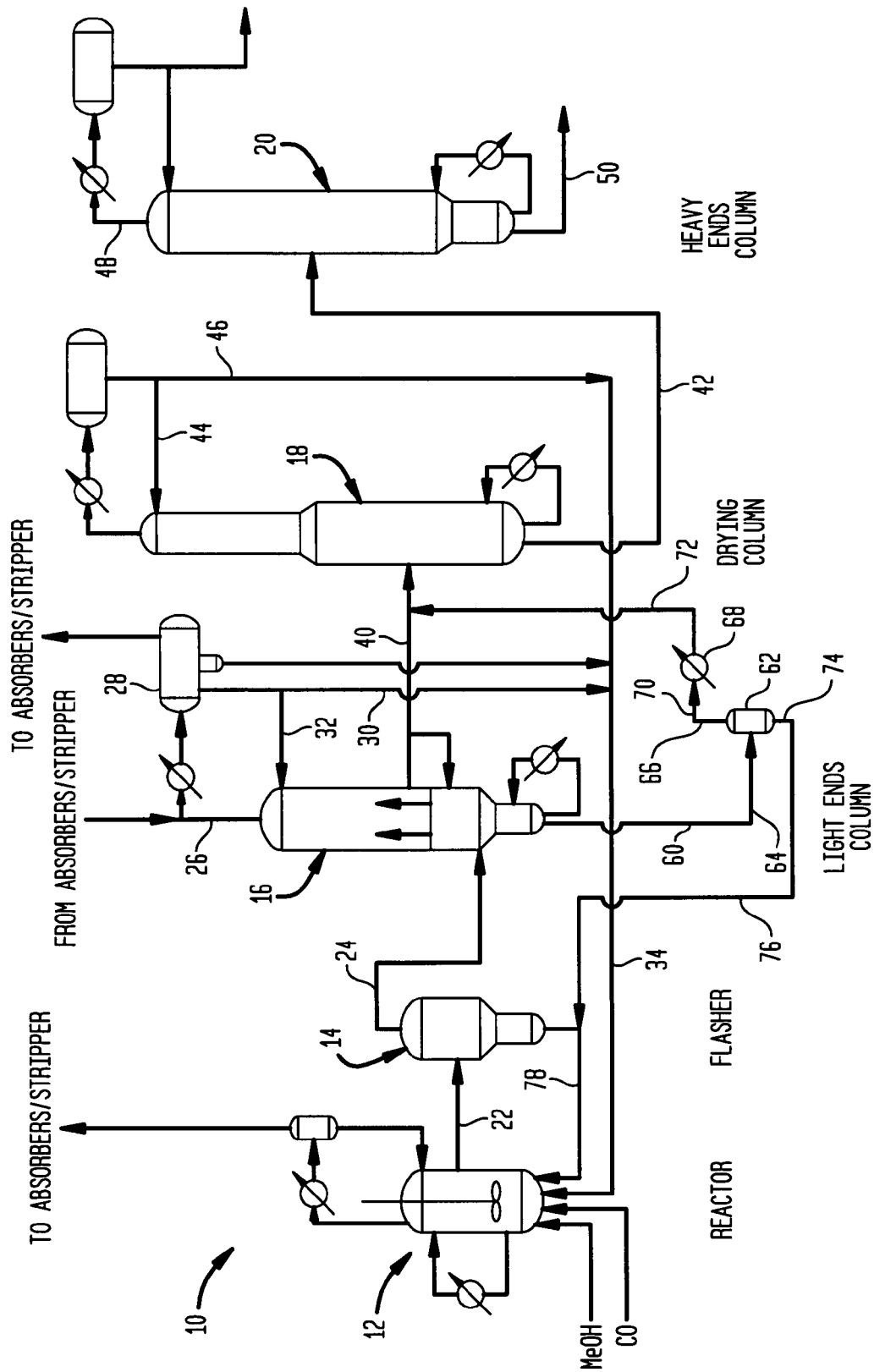
FIG. 2 is a schematic diagram showing an apparatus of the invention wherein a flash vessel is provided on the residue stream of a light ends column of an acetic acid unit.

Referring to FIG. 2, there is shown a carbonylation unit 10 of the present invention. Unit 10 includes a reactor 12, a flasher 14, a light ends column 16, a drying or dehydration column 18 as well s a heavy ends column 20. Reactor 12 includes the reaction medium and there is fed thereto methanol and carbon monoxide. A portion of the reaction medium is continuously provided to flasher 14 via line 22 where crude product is flashed and sent to light ends column 16 via line 24 as a hot vapor feed.

A gaseous purge stream is typically vented from the head of the reactor to prevent buildup of gaseous by-products such as methane, carbon dioxide, and hydrogen and to maintain a set carbon monoxide partial pressure at a given total reactor pressure. Optionally (as illustrated in Chinese Patent No. ZL92108244.4), a so-called "converter" reactor can be employed which is located between the reactor and flash vessel (14, 114) shown in FIGS. 2 and 3. The "converter" produces a vent stream comprising gaseous components which are typically scrubbed with a compatible solvent to recover components such as methyl iodide and methyl acetate. The gaseous purge streams from the reactor and converter can be combined or scrubbed separately and are typically scrubbed with either acetic acid, methanol or mixtures of acetic acid and methanol to prevent loss of low boiling components such as methyl iodide from the process. If methanol is used as the vent scrub liquid solvent, the enriched methanol from the scrubbing system is typically returned to the process by combining with the fresh methanol feeding the carbonylation reactor—although it can also be returned into any of the streams that recycle back to the reactor such as the flasher residue or light ends or dehydration column overhead streams. If acetic acid is used as the vent scrub liquid solvent, the enriched acetic acid from the scrubbing system is typically stripped of absorbed light ends and the resulting lean acetic acid is recycled back to the absorbing step. The light end components stripped from the enriched acetic acid scrubbing solvent can be returned to the main process directly or indirectly in several different locations including the reactor, flasher, or purification columns. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well within the scope of the present invention as will be appreciated from the appended claims and the description which follows.

In column 16, the product is purified of light components which exit the column via line 26, are condensed in a decanter 28 and refluxed via line 32 or returned to the reactor via lines 30, 34. Also provided, but not shown, are absorbers and strippers used to recycle material into the system.

A purified product stream 40 is withdrawn as a (preferably liquid) sidestream from column 16 and fed to drying column 18 where water is removed from the partially purified product. Thereafter, the dried product is provided to heavy ends column 20 via line 42, while the overhead and same product acetic acid is used as reflux for column 18 via line 44 or recycled to the reactor via lines 34, 46. Product acetic acid is taken overhead from heavy ends column 20 via line 48, while heavy waste is removed via line 50.

Column 16 generates a liquid residue stream 60 which is conventionally recycled with residue from the flasher; however, in accordance with the invention, stream 60 is provided to a flash unit 62 via line 64 where the stream encounters a reduced pressure so that stream 60 is at least partially vaporized such that flash unit 62 provides a second vapor product stream 66 which is fed to a condenser 68 via line 70. Stream 66 is condensed at 68 and subsequently combined with stream 40 via line 72. The combined stream is then fed forward to column 18 as shown and further purified as described above. Instead of condensing stream 66, the stream could be compressed and fed forward as hot vapor.

A liquid residue stream 74 exits flash unit 62 and is recycled back to the reactor with the residue from flasher 14 via lines 76, 78.

A portion of the acetic acid in stream 60 is thus recovered by flash unit 62 and fed forward in the system, reducing the hydraulic lead on column 16 and increasing productivity. Typically, stream 60 comprises between about 90 wt. % acetic acid to about 99 wt. % acetic acid and preferably at least 90 wt. % or at least 95 wt. %. Depending upon the operating pressure of flash unit 62, at least 10%, at least 20%, at least 30% or at least 40% of the acetic acid in stream 60 may be recovered.

The system of FIG. 1 was simulated by an empirical computer model to ascertain the effects of pressure in flash unit 62 on acid recovery and column loading using a fully loaded (incipient flooding) base case with no flash unit. Results appear in Table 1.

TABLE 1

Recovery of Acetic Acid from Light Ends (LE)
Column Residue by Simple Flash

| Pressure of Light Ends Residue Treatment Flash Vessel (psia) | Fraction of Acetic Acid Recovered from LE Residue | Maximum Tray Flood Factor Relative to Operation With No Flash Unit on Light Ends Column |
|---|---|---|
| No flash | 0 | 1 |
| 20 | 0.194 | 0.990 |
| 15 | 0.244 | 0.987 |
| 10 | 0.308 | 0.984 |
| 5 | 0.404 | 0.979 |
| 3 | 0.466 | 0.976 |

It is seen in Table 1 that over 40% of the acetic acid in the light ends column residue stream is recovered and the hydraulic loading of the light ends column was reduced substantially. These results are shown graphically in FIG. 1, discussed above.

Figure 3:
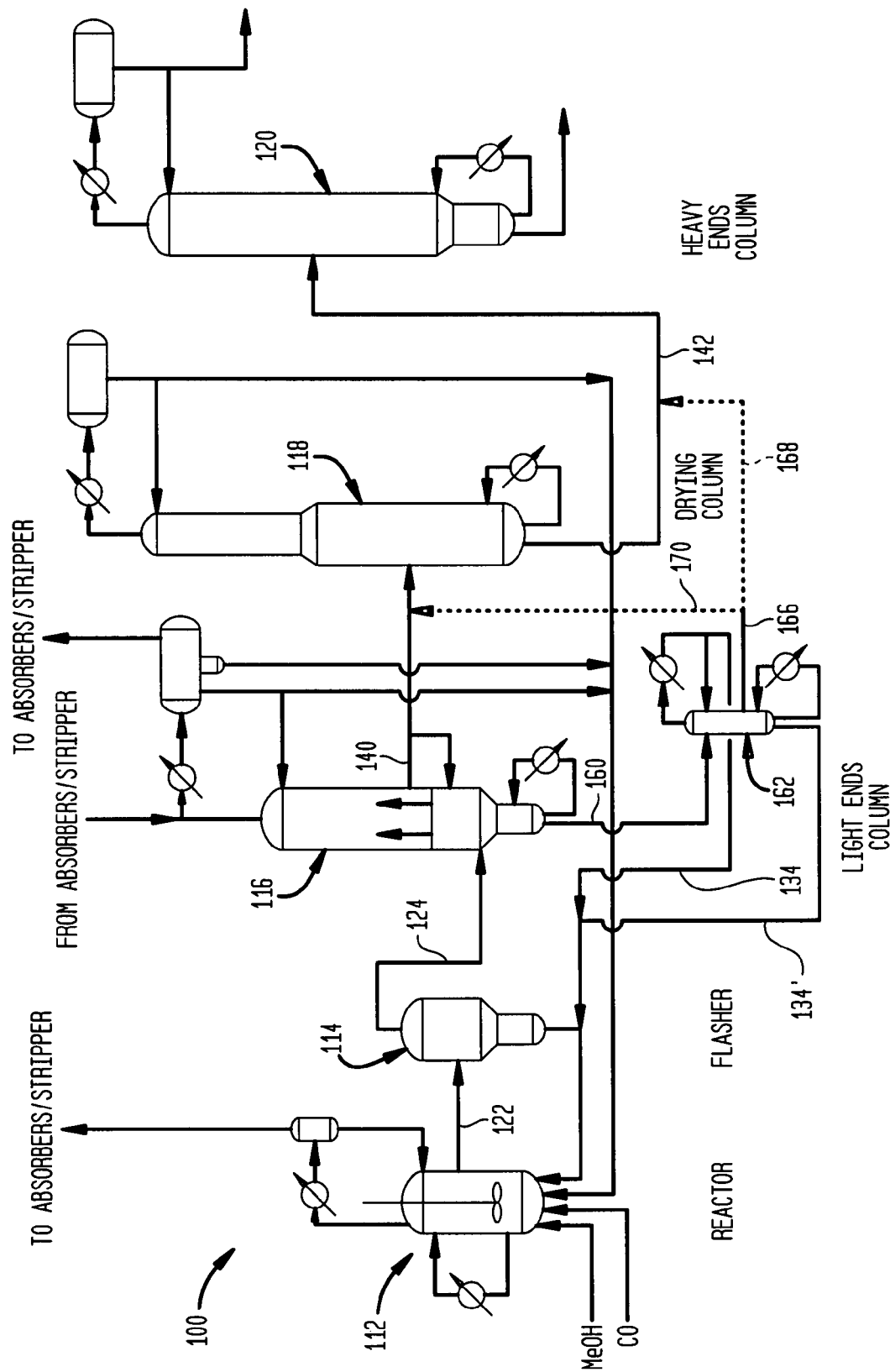
FIG. 3 is a schematic diagram showing an apparatus of the invention wherein a distillation column is provided on the residue stream of a light ends column of an acetic acid unit.
Figure 4:
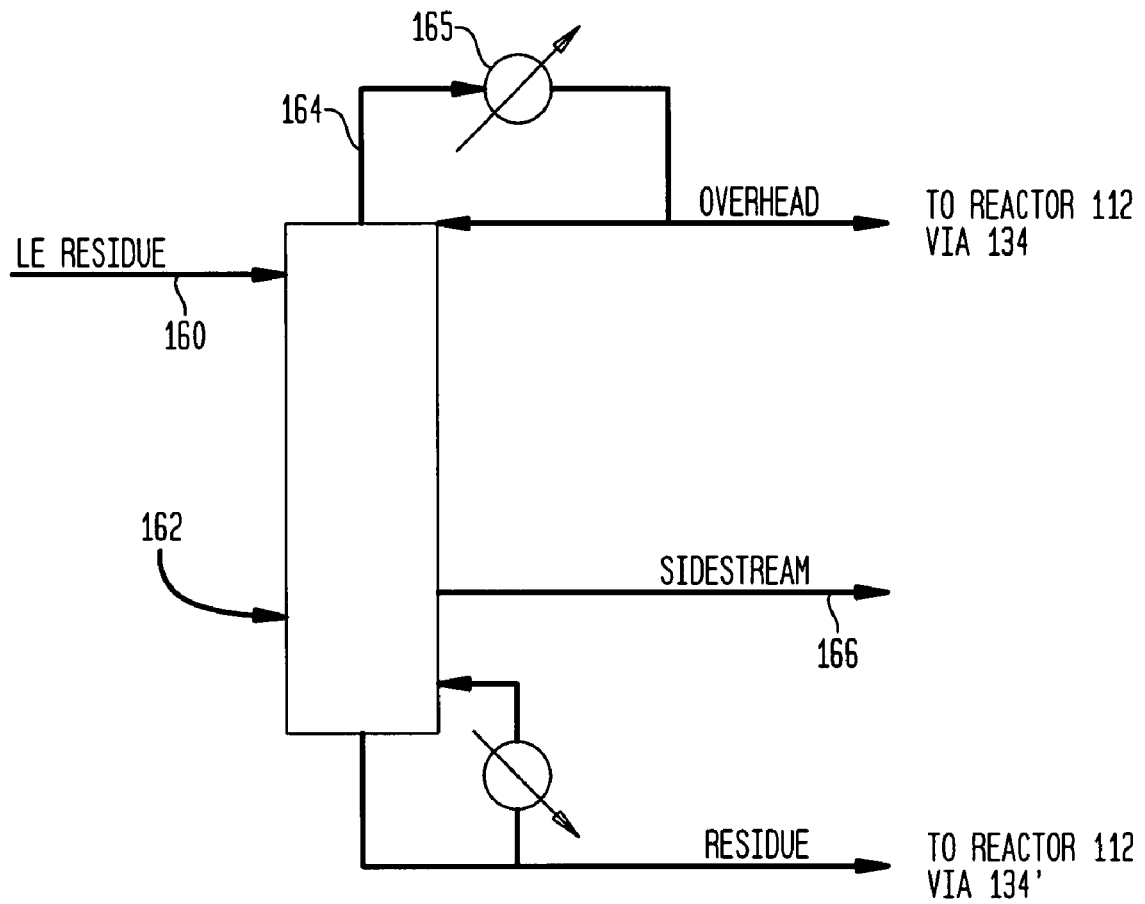
FIG. 4 is a schematic diagram of a stripper-type distillation column which may be used on the residue stream of a light ends column of an acetic acid unit in accordance with the invention.

Referring to FIGS. 3 and 4, there is shown another carbonylation unit 100 of the invention which includes a reactor 112, a flasher 114, a light ends column 116, a drying or dehydration column 118, and a heavy ends column 120. The various parts operate as described above in connection with like components to produce acetic acid and are connected via lines 122, 124, 140, and 142 and so forth as shown in FIG. 3.

Instead of a flash unit, there is provided an additional distillation column 162 which is fed by liquid residue stream 160 from light ends column 116. Column 162 generates an overhead stream 164 which may be condensed at 165 and used as reflux in the column or returned to reactor 112, as well as product sidestream 166 which may be condensed or compressed and fed forward via line 168 or 170 and combined with a first product stream prior to the drying column or combined with the first product stream prior to the heavy ends column. Provided stream 166 is of sufficient quality, it is preferable to feed the stream directly to the heavy ends column (that is, feed the stream forward without further water removal), since this will also reduce the hydraulic load on dehydration column 118. If so desired, methanol may be added to column 162 to reduce inorganic iodides in the product stream as is known in the art. Likewise, column 162 may be operated without a condensed reflux stream such that it operates as a stripper-type distillation column if so desired.

Utilizing an empirical computer model, distillation column 162 was simulated in order to ascertain its ability to recover acetic acid from a light ends column residue stream. A light ends column residue sample was also distilled in a laboratory unit having the configuration of column 162. Results are compared in Table 2.

TABLE 2

Comparison of Computer Model and Laboratory Results

|  | Computer Model Results | Laboratory Distillation Results |
|---|---|---|
| Sidestream Flow as Fraction of LE Residue Flow | 0.477 | 0.424 |
| Overhead Flow as Fraction of LE Residue Flow | 0.332 | 0.289 |
| Residue Flow as Fraction of LE Residue Flow | 0.191 | 0.132 |
| Light Ends Column Loading Relative to Current Operation | 0.984 |  |
| Drying Column Loading Relative to Current Operation | 0.968 |  |

It is seen in Table 2 that the empirical model agreed well with the laboratory data and that recovery from the liquid residue stream was over 40%. Hydraulic load on the light ends column is substantially reduced and, in the case shown where recovered acid is fed forward downstream of the dehydration column, hydraulic load on the dehydration column is also substantially reduced.

The invention has been described in detail and illustrated in connection with numerous embodiments. Modifications to specific embodiments within the spirit and scope of the present invention will be readily apparent to those of skill in the art. Such modifications are within the spirit and scope of the present invention which is set forth in the appended claims.

What is claimed is:

1. A carbonylation process for producing acetic acid comprising:
   (a) carbonylating methanol or its reactive derivatives in the presence of water, a catalyst selected from rhodium catalysts, iridium catalysts and mixtures thereof, and a methyl iodide promoter to form an acetic acid reaction mixture in a reactor;
   (b) providing a portion of the acetic acid reaction mixture to a flash vessel wherein the acetic acid mixture is separated into a liquid recycle stream and a first crude product stream;
   (c) recycling the liquid recycle stream back to the reactor and feeding the first crude product stream to a light ends column;
   (d) distilling the first crude product stream to remove low boiling components to produce purified first product stream and a liquid residue stream, wherein the liquid residue stream comprises acetic acid;
   (e) vaporizing a portion of the liquid residue stream to produce a second product stream from the liquid residue stream and a residual liquid residue stream;
   (f) recycling the residual liquid residue stream back into the reactor and
   feeding the second product stream forward in the process for further purification to produce acetic acid.

2. The method according to claim 1, wherein the step of feeding the second product stream forward in the process for further purification to produce acetic acid comprises the step of condensing the second product stream.

3. The method according to claim 1, wherein the step of feeding the second product stream forward in the process for further purification to produce acetic acid comprises the step of compressing the second product stream.

4. The method according to claim 1, wherein the step of feeding the second product stream forward in the process for further purification to produce acetic acid comprises the step of combining the purified first product stream and the second product stream.

5. The method according to claim 4, wherein the purified first product stream and the second product stream are combined and thereafter treated in a drying column.

6. The method according to claim 1, wherein the step of feeding the second product stream forward in the process for further purification to produce acetic acid comprises the steps of further purifying the purified first product stream and the second product stream.

7. The method according to claim 6, wherein the purified first product stream and the second product stream are fed to a single dehydrating column.

8. The method according to claim 1, wherein at least 10% of the acetic acid present in the liquid residue stream is vaporized from the liquid residue stream to produce the second product stream.

9. The method according to claim 1, wherein at least 20% of the acetic acid present in the liquid residue stream is vaporized from the liquid residue stream to produce the second product stream.

10. The method according to claim 1, wherein at least 30% of the acetic acid present in the liquid residue stream is vaporized from the liquid residue stream to produce the second product stream.

11. The method according to claim 1, wherein at least 40% of the acetic acid present in the liquid residue stream is vaporized from the liquid residue stream to produce the second product stream.

12. The method according to claim 1, wherein the liquid residue stream comprises at least 90% by weight of acetic acid.

13. The method according to claim 1, wherein the liquid residue stream comprises at least 95% by weight of acetic acid.

14. The method according to claim 1, wherein the liquid residue stream comprises from about 90% by weight to about 99% by weight of acetic acid.

15. A carbonylation process for producing acetic acid comprising:

(a) carbonylating methanol or its reactive derivatives in the presence of water, a catalyst selected from rhodium catalysts, iridium catalysts and mixtures thereof, and a methyl iodide promoter to form an acetic acid reaction mixture in a reactor;
(b) providing a portion of the acetic acid reaction mixture to a flash vessel wherein the acetic acid reaction mixture is separated into a liquid recycle stream and a first crude product stream;
(c) recycling the liquid recycle stream back to the reactor and feeding the first crude product stream to a light ends column;
(d) distilling the first crude product stream in the light ends column to remove low boiling components to produce a purified first product stream and a liquid residue stream, wherein the liquid residue stream comprises acetic acid;
(e) directing the liquid residue stream to a second distillation column and distilling the liquid residue stream to generate an overhead stream which is condensed and utilized as reflux in the second distillation column and/or is recycled back to the reactor, a second purified product stream, and a second liquid residue stream; and
(f) recycling the second liquid residue stream back into the reactor and feeding the second purified product stream forward in the process for further purification to produce acetic acid.

16. The method according to claim 15, wherein the step of feeding the second purified product stream forward in the process to produce acetic acid comprises the step of removing iodide from the second purified product stream.

17. The method according to claim 16, wherein the step of removing iodide from the second purified product stream comprises adding methanol to the second purified product stream.

18. The method according to claim 15, wherein the step of feeding the second purified product stream forward in the process to produce acetic acid does not include further removal of water from the second purified product stream.

* * * * *